(12) United States Patent
Cichocki

(10) Patent No.: US 8,128,656 B2
(45) Date of Patent: Mar. 6, 2012

(54) DEVICE FOR CREATING AND MAINTAINING INFUSION PASSAGES IN TISSUE

(75) Inventor: Frank R. Cichocki, Easton, PA (US)

(73) Assignee: Ethicon, Inc., Somerville, NJ (US)

( * ) Notice: Subject to any disclaimer, the term of this patent is extended or adjusted under 35 U.S.C. 154(b) by 1349 days.

(21) Appl. No.: 11/235,853

(22) Filed: Sep. 27, 2005

(65) Prior Publication Data

US 2006/0030883 A1    Feb. 9, 2006

Related U.S. Application Data

(63) Continuation-in-part of application No. 11/142,589, filed on Jun. 1, 2005, now abandoned, which is a continuation-in-part of application No. 10/909,717, filed on Aug. 2, 2004, now Pat. No. 7,875,055, which is a continuation of application No. 10/727,367, filed on Dec. 4, 2003.

(51) Int. Cl.
*A61B 17/04* (2006.01)
*A61M 31/00* (2006.01)

(52) U.S. Cl. ..................................... 606/228; 604/93.01

(58) Field of Classification Search .................. 606/228, 606/108, 222; 128/898; 604/272–274, 541–543
See application file for complete search history.

(56) References Cited

U.S. PATENT DOCUMENTS

| | | | |
|---|---|---|---|
| 3,212,502 A | 10/1965 | Myers | |
| 3,474,703 A | 10/1969 | Davis | |
| 3,821,956 A | 7/1974 | Gordhamer | |
| 3,918,455 A | 11/1975 | Coplan | |
| 4,159,720 A | * 7/1979 | Burton | ........................ 424/423 |
| 4,232,673 A | 11/1980 | Bucalo | |

(Continued)

FOREIGN PATENT DOCUMENTS

FR    2747908    * 4/1996

(Continued)

OTHER PUBLICATIONS

International Search Report dated Jun. 10, 2005 for corresponding Appln. No. PCT/US2004/040488.

*Primary Examiner* — Tuan Nguyen (74) *Attorney, Agent, or Firm* — E. Richard Skula (57) ABSTRACT

Methods and devices are disclosed for the in-vivo creation and maintenance of contiguous fluid passages in tissue through the use of tissue buttressing portions with interrupted perimeter walls. These portions can be formed from hollow fiber or extruded components. One end of the tissue-buttressing portion is connected to a hollow tube, which may be connected to a fluid source. The other end of the buttressing portion may be attached to a needle or other device suitable for the penetration of tissue and the formation of passageways in tissue. When the device is installed in tissue, the hollow tube portion of the device is passed part way through the surface of the patient and serves as the conduit for the transfer of fluid to the implanted tissue-buttressing portion of the device. The presence of the buttressing portion within the tissue causes a bridging of the local tissue thereby forming an infusion passage between the external surface of the buttressing portion and the abutting tissue. Therapeutic fluids may be passed from the hollow fiber conduit of the device and though the infusion passage created by the buttressing portion of the device and the surrounding tissue.

5 Claims, 7 Drawing Sheets

U.S. PATENT DOCUMENTS

| | | | |
|---|---|---|---|
| 4,650,473 A * | 3/1987 | Bartholomew et al. | 604/174 |
| 4,673,565 A | 6/1987 | Di Luccio | |
| 4,712,553 A | 12/1987 | MacGregor | |
| 5,100,379 A | 3/1992 | Wendell | |
| 5,458,582 A | 10/1995 | Nakao | |
| 5,538,735 A | 7/1996 | Ahn | |
| 5,735,829 A | 4/1998 | Cherian | |
| 5,797,886 A | 8/1998 | Roth | |
| 5,836,962 A | 11/1998 | Gianotti | |
| 5,891,101 A | 4/1999 | Wilcox | |
| 5,919,473 A * | 7/1999 | Elkhoury | 424/422 |
| 5,984,933 A | 11/1999 | Yoon | |
| 6,152,141 A | 11/2000 | Stevens | |
| 6,264,500 B1 | 7/2001 | Kawabe | |
| 6,350,253 B1 * | 2/2002 | Deniega et al. | 604/164.02 |
| 6,368,315 B1 | 4/2002 | Gillis | |
| 6,520,949 B2 | 2/2003 | St. Germain | |
| 6,565,534 B1 | 5/2003 | Winters | |
| 6,626,885 B2 | 9/2003 | Massengale | |
| 2002/0029066 A1 | 3/2002 | Foerster | |
| 2002/0095133 A1 | 7/2002 | Gillis | |
| 2003/0028204 A1 | 2/2003 | Li | |
| 2005/0125034 A1 | 6/2005 | Cichocki | |
| 2006/0030883 A1 | 2/2006 | Cichocki | |

FOREIGN PATENT DOCUMENTS

| | | |
|---|---|---|
| FR | 2747908 A | 10/1997 |
| GB | 1528955 A | 10/1978 |
| WO | 01/05210 A2 | 1/2001 |
| WO | 01/05210 A3 | 7/2001 |
| WO | 03/017854 A1 | 3/2003 |

* cited by examiner

DEVICE FOR CREATING AND MAINTAINING INFUSION PASSAGES IN TISSUE

RELATED PATENT APPLICATIONS

This application is a continuation-in-part application of Ser. No. 11/142,589 filed on Jun. 1, 2005, now abandoned, which is a continuation-in-part of application Ser. No. 10/909,717, filed on Aug. 2 2004, now U.S. Pat. No. 7,875,055, which is a continuation of application Ser. No 10/727,367, filed on Dec. 4, 2003, the contents of which are incorporated herein in their entirety.

FIELD OF INVENTION

The present invention generally relates to surgical devices for the infusion of therapeutic fluids into tissue and methods of implantation for said surgical devices.

BACKGROUND OF INVENTION

Patients may benefit from the infusion of therapeutic fluids into tissues surrounding a wound in a variety of ways. Local anesthetics may be infused directly to the wound site to help manage pain post-operatively. Antibiotics may be infused to a wound site to eliminate infections. Growth factors or oxygen rich fluids may be infused to facilitate wound healing and recovery. A variety of other active agents including but not limited to chemotherapeutics, stems cells, hemostatic agents, angiogenic, and anti-angiogenic agents may also provide patient benefit when delivered locally to tissues via infusion.

Traditional infusion devices are fabricated with a contiguous lumen that generally extends from the fluid source and along the entire length of the device to the tissues intended to receive the fluid. The lumen is typically formed as a continuous hollow element through extrusion or other processes, and ordinarily has a solid wall that contains exits or ports for fluid egress. If the device is intended to deliver a fluid over an extended distance within tissue, multiple ports or exits are formed along the axis of the device in an attempt to distribute the fluid from the lumen along the implanted length of the device.

For example, U.S. Pat. No. 3,821,956 to Gordhamer discloses a device for the dilation and treatment of a bovine teat. The device is hollow and has a spiral groove on the external surface of the device. There are exit ports that extend from the inner lumen of the device to the external groove. This device appears to be relatively inflexible.

In U.S. Pat. No. 4,159,720, a method of treating tissue with a device comprised of a wicking material that may be implanted in a wound is disclosed. This reference describes that the wicking material may be a hollow monofilament provided with lateral perforations through which the fluid will pass into the tissue. Alternatively, the wicking material is described as being a solid filament having spiral or longitudinal grooves in its external surface. This patent further describes the concept of attaching a suture needle directly to the wicking material to facilitate implantation of the device in tissue. For example, this reference discloses that the wick may be installed into position as if it were a suture, and in one embodiment, the wick may serve as a suture for holding the severed flesh together as well as a carrier or conduit for delivering fluid to the affected area.

U.S. Pat. No. 5,458,582 to Nakao describes an anesthesia delivery device comprising an elongate flexible tubular member in the form of a hollow tube made of bioabsorbable material, the tubular member having a proximal end portion with a continuous cylindrical side wall and a distal end portion provided with a plurality of apertures spaced longitudinally along the distal end portion.

Similarly, U.S. Pat. No. 6,626,885 describes an infusion catheter exhibiting a plurality of apertures located along the implantable segment, and a method of implantation with an auxiliary tissue-penetrating device, whereby the infusion catheter is introduced via the auxiliary tissue-penetrating device through skin adjacent to an incision site. It is generally accepted by the medical community that using a catheter entry site remote from the incision site reduces the risk of infection associated with the use of a catheter that is left in place over a period of time.

However, there are several problems associated with the approaches described in the prior art for the delivery of fluids transcutaneously. The first problem is associated with the formation of exit ports from the device. The creation of the ports requires the machining of the tube through processes such as drilling, punching, laser cutting or other suitable methods. Many of these processes are intrinsically difficult and costly, Additionally, these processes typically become more difficult and costly to implement as the diameter of the catheter decreases, with most traditional infusion catheters exhibiting large diameters in excess of 0.020".

An additional problem of these tubular devices is that they are ordinarily smooth along the external surface. The smooth surface abuts the surrounding tissues and forms a lightly sealed surface surrounding the exit ports. This effect can result in an increase in the pressure differential from within the tube to overcome this sealing effect to enable fluid egress from the device.

In view of the drawbacks associated with the infusion devices described above, it is desirable to have an infusion device where the infusion passage is maintained in a continuous fashion from the point of fluid egress to the terminus of the device in the tissue, thereby enabling the egress of fluid from the device into the surrounding tissue along the full length of the implanted device.

SUMMARY OF INVENTION

The invention enables the transcutaneous delivery of fluids to a patient through a device comprised of a first length of hollow tube and a tissue-buttressing portion with discontinuous circumferential surfaces. Implantation of said device in tissue can be facilitated through use of a leading needle. Once positioned, the device can be anchored through the use of knots. The present invention overcomes the difficulties described above in that the tissue-buttressing portion of the device maintains an infusion passage and enables the egress of fluid from the device and into the surrounding tissue along its entire length.

BRIEF DESCRIPTION OF THE DRAWINGS

FIG. 4a-5c show cross-sections of the tissue-buttressing portion; and

FIGS. 6a-7c depict implantation techniques using the described device.

DETAILED DESCRIPTION OF INVENTION

For the majority of applications under consideration, the tissue will surround and make intimate contact with the infusing segment of the device. As used herein, the term "tissue-buttressing" means the act of maintaining a space within the tissue surrounding the infusion device in such a manner as to enable fluid to be transported and emitted along that segment of the device designated as the "tissue-buttressing" portion.

Figure 1:
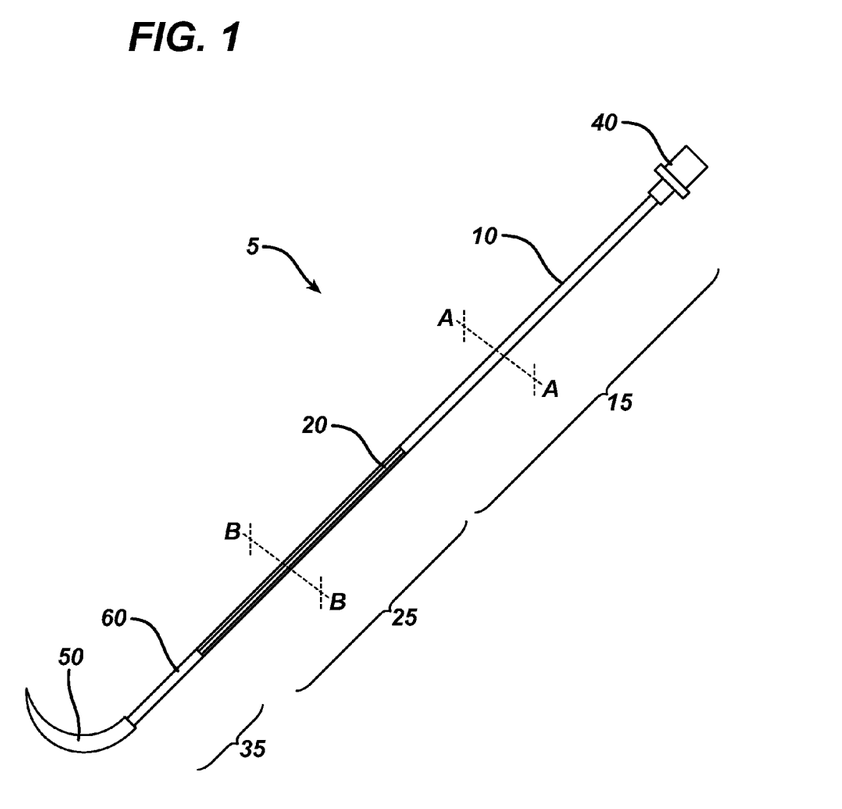
FIG. 1 is a perspective view of one embodiment of the device in accordance with the present invention.

Referring to FIG. 1, the device 5 comprises an elongate flexible tubular member with a proximal end portion 15, a tissue-buttressing portion 25 and an optional distal end portion 35. The proximal end portion 15 has a continuous cylindrical sidewall 10 and the distal end portion 35 has a cylindrical sidewall 60. The tissue-buttressing portion 25 has a channel 20, which interrupts its sidewall. The tissue-buttressing portion may be comprised of hollow tubes with interrupted sidewalls. Alternatively, the tissue-buttressing portion 25 may be comprised of a plurality of tissue-buttressing tubes each having a channel 20 that interrupts its sidewalls, where the plurality of tubes is joined at one end to the proximal end portion 15, and the optional distal end portion 35 or a suture needle 50 on the other end.

This tissue-buttressing portion 25 acts to maintain a passage in tissue, thereby enabling the transport of fluids along its length within tissue. It can be a variety of lengths to accommodate a wide range of sites to be treated depending on the surgical procedure, and can vary from 3 cm to 35 cm. The tissue-buttressing portion may optionally transition back to a distal end portion 35, which comprises a continuous cylindrical sidewall portion 60 distal to the channel 20. A suture needle 50 is attached to the distal end portion 35, which facilitates the creation of infusion passages and/or provides a means of implantation in surgical incisions. Alternatively, the suture needle may be attached to the distal end of the tissue-buttressing portion 25.

The suture needle may be either straight or curved, depending on the particular procedure to be performed. Curved needles offer the surgeon the ability to easily and accurately weave the device through various tissue planes. Additionally, a curved needle facilitates the formation of a knot at the distal end of the cylindrical side wall 60 or the distal end of the tissue-buttressing portion 25. Said knot may be used to prevent the accidental dislodgment of the infusion device from a wound or implantation site. Straight needles may be used when it is desirable to form a tunnel or tissue passage over a long distance beneath the skin or other tissue plane, such as between subcutaneous tissue and fascia, or between fascia and peritoneum. When it is desirable to penetrate the skin at a substantial distance from the wound site before drawing the device into the wound, a straight needle would be advantageous. Also, when it is desirable to implant the device along a tissue plane for an extended distance without implanting any portion of said device in an incision, a straight needle may be used. As such, a straight needle may also be preferred in certain laparoscopic procedures. Additionally, a variety of needle point designs may be used to optimize surgeon control and/or minimize the size of the hole produced in the various tissues. Needle point designs may include, but are not limited to: cutting edge, taper point, taper cut, and blunt point and may be selected according to the operative procedure and technique to be practiced.

One or more elongate flexible tubular member may be connected to the suture needle by techniques well known in the art of needle and suture making, including, but not limited to mechanical swaging and adhesive attachment.

The proximal end portion of the one or more elongate flexible tubular members may be directly connected to a fluid source (not shown), or alternately may be attached to an adapter 40 that enables connection to a fluid source, as shown in FIG. 1. This adapter 40 may be of any standard or non-standard design commonly used in the field of medicine including, but not limited to, male or female luer lock fittings, twist-lock connectors, or press-fit connectors. The proximal end portion 15, the distal end portion 35, and the tissue-buttressing portion 25 can all have a diameter equal to that of a suture thread, although smaller or larger diameters may also be used. This can practically range from about 0.005" to about 0.030".

The proximal end portion, distal end portion, and tissue-buttressing portion of the device may be produced from a variety of polymer systems, including but not limited to polyglycolic acid (PGA), polylactic acid (PLA), PGA/PLA copolymers, polycaprolactone (PCL), PCL/PGA copolymers, polydioxanone, trimethylcarbonate (TMC), polyproylene, polyamide, polytetraflouroethylene (PTFE), and polyethylene.

Figure 2A:
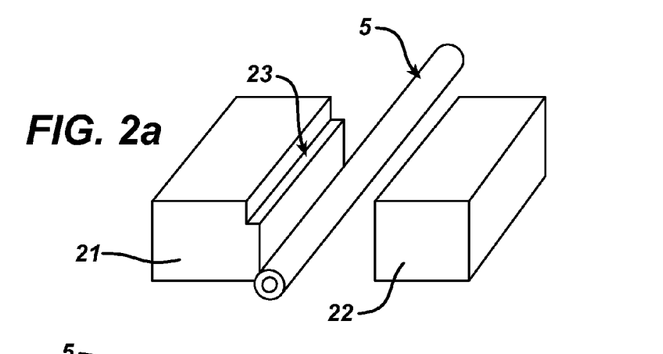
FIG. 2a-2d depict a method of manufacturing the channel in the tissue-buttressing portion of the device.
Figure 2B:
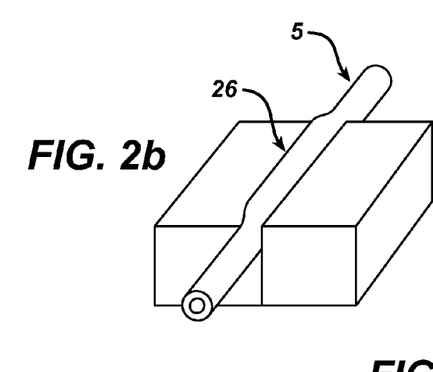
Figure 2C:
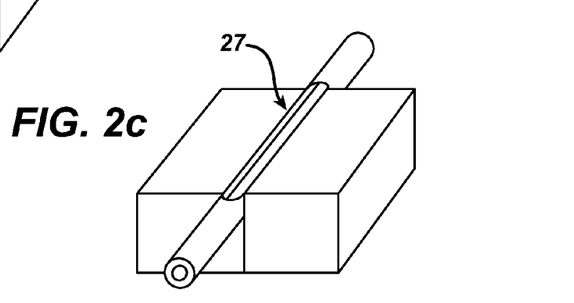
Figure 2D:
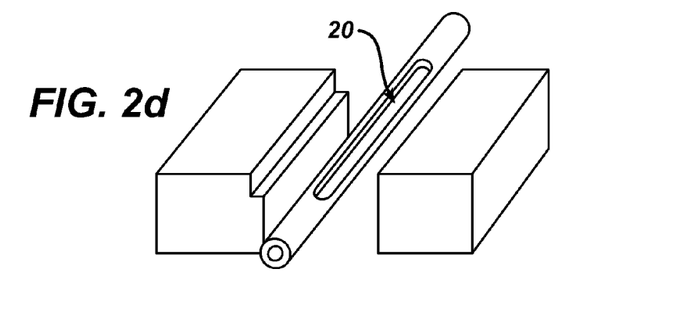

The tissue-buttressing portion 25 shown in FIG. 1 may be fabricated in a number of ways. In one embodiment, a hollow tube is extruded using standard extrusion and optional drawing techniques known to those skilled in the art. The channel 20 is fabricated by removing a portion of the hollow tube to produce a single continuous channel 20 along a specified length of the distal end. Sharp cutting instruments such as razor blades, knives, or various shearing instruments may be used to section and remove a portion of the hollow extrusion. Alternatively laser light may be used to produce a channel or slit along a specified length of the tube. To facilitate removal of a portion of the hollow extrusion, fixtures that compress a portion of the hollow extrusion may be used as shown in FIGS. 2a through 2d. Referring now to FIG. 2a, mating die components 21 and 22, with one or more of the dies exhibiting a recess or ledge 23, may be used to compress the hollow tube 5. A portion of the hollow tube is then forced above the top plane formed by the mating dies in a predominantly flattened form 26, as shown in FIG. 2b. The portion of the tube extending above the top plane of the dies 26 may then be cut away from the tube by sliding a sharp cutting instrument along the top surfaces of the mating dies. Cutting instruments may include but are not limited to knives, razor blades, die punches. In this way the cutting action removes tube material to a depth equal to or greater than the lumen wall thickness. At this step the tube will appear as represented in FIG. 2c with a continuous slit 27 spanning the full length of the constrained portion of the tube. The components of the die are opened to release the tube, as shown in FIG. 2d, and the tubing material recovers elastically to a cylindrical shape with a channel 20.

Figure 3A:
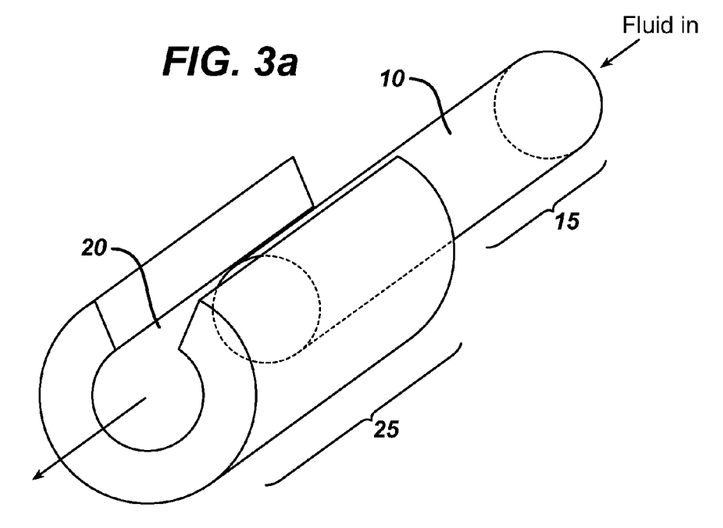
FIG. 3a-3b is representative of attachment means of the tissue buttressing portion and proximal portion of the present invention.
Figure 3B:
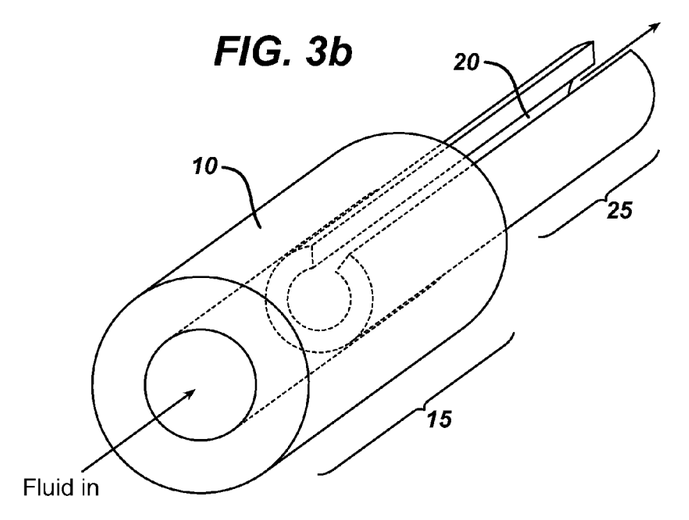

FIGS. 3a and 3b show alternate embodiments of fabricating the tissue-buttressing portion 25. This tissue-buttressing portion 25 may be formed as a separate part utilizing the techniques described above, then joined together to the continuous cylindrical sidewall portions 10 and/or 60 of proximal portion 15 and/or distal end portion 35. Referring to FIG. 3a, the outer diameter of the proximal end portion 15 is smaller in diameter than the inside diameter of the tissue-buttressing portion 25 and therefore is positioned at least partially into the inner diameter of proximal end portion 15. Referring now to FIG. 3b, the outer diameter of the tissue-buttressing portion 25 is smaller in diameter than the inside diameter of the proximal end portion 15 and therefore the tissue-buttressing portion 25 is positioned at least partially into the inner diameter of the proximal end portion 15. In either embodiment, fluid flows through the continuous cylindrical sidewall portion 10 of proximal end portion 15 and into the channel 20 of tissue-buttressing portion 25. Insertion of the proximal end portion 15 into the tissue-buttressing portion 25, as shown in FIG. 3a, or vice versa, as shown in FIG. 3b, followed by application of thermal energy at the site where the two portions overlap will yield a functional device. Sources of thermal energy that may be employed may include, but are not limited to: heated dies, ultrasonic welding horns, friction welding equipment, and radio frequency sources. Alternatively, adhesives may be used to join the tissue-buttressing portion and the proximal and/or distal end portions 15 and 35. In any case, the adhesive must be biocompatible and in some cases preferably bioabsorbable.

Figure 4A:
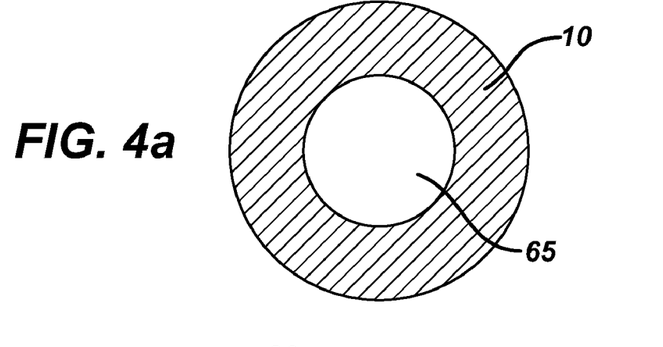
Figure 4B:
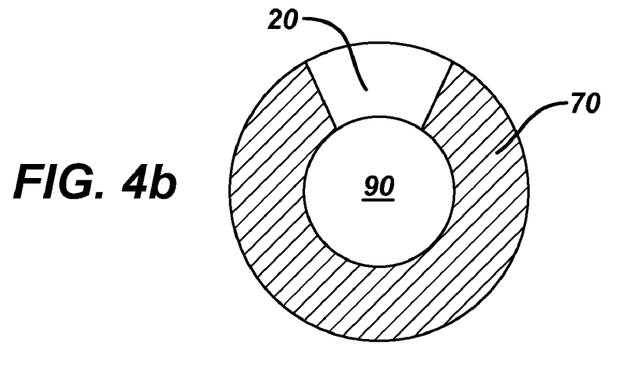
Figure 4C:
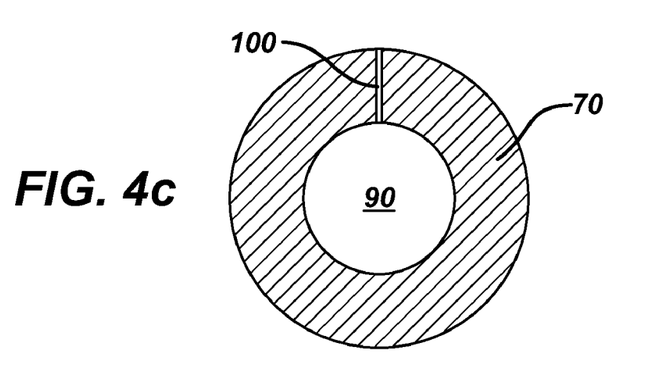
Figure 4D:
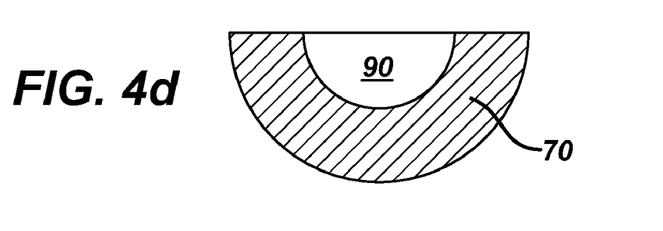

A schematic representation of the cross-section of the proximal end portion 15 shown in FIG. 1 along A-A in its simplest form is shown in FIG. 4a. The cylindrical sidewall 10 and lumen 65 of the extrusion are both continuous. A schematic representation of one embodiment of the cross-section of the tissue-buttressing portion 25 and channel 20 shown in FIG. 1 along slice B-B is shown in FIG. 4b. The wall of the extrusion 70 is interrupted by a channel 20 that is in fluid communication with the lumen 90 of the tissue-buttressing portion 25. The width of the channel may vary from a fine slit 100 with a width that is microscopic in dimension, as depicted in FIG. 4c, to a half-circle or c-shape as schematically depicted in FIG. 4d.

Figure 5A:
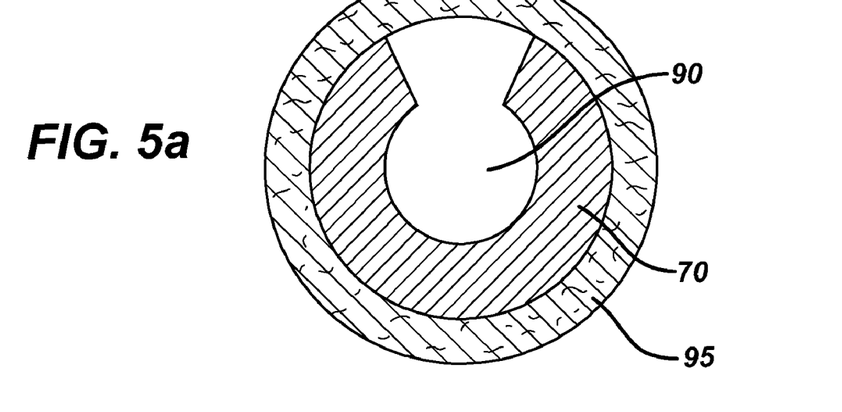
Figure 5B:
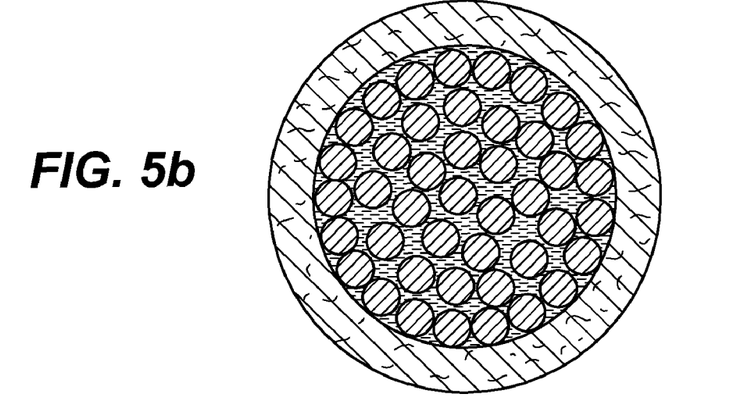
Figure 5C:
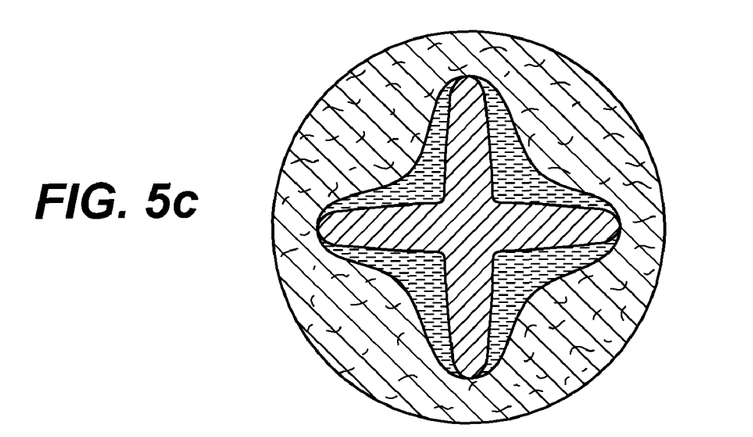

The manner in which these various tissue-buttressing elements may function in tissue is schematically depicted in FIGS. 5a, 5b and 5c. A cross-sectional schematic representation of a tissue-buttressing element 70 comprised of a hollow extrusion with a continuous channel through the wall of the extrusion is shown in FIG. 5a. The surrounding tissue 95 is prevented from collapsing and closing the passage by this rigid form. Moreover, the lumen of the hollow extrusion and the channel through the wall of the hollow extrusion combine to provide a passage for the transport of fluid along the entire length of the tissue buttressing segment 70.

A cross-sectional schematic representation of a tissue-buttressing element comprised of a plurality of solid fibers is shown in FIG. 5b. As the surrounding tissue closes around the plurality of filaments, said filaments contact one another, leaving open space or interstice between the contact points of the individual filaments. Fluids may pass through these interstices and contact the surrounding tissue at the periphery of the fiber bundle along the entire length of said fiber bundle.

A cross-sectional schematic representation of a tissue-buttressing element comprised of a cross-shaped buttress is shown in FIG. 5c. As tissue closes around this buttress it is prevented from conforming to the interior surfaces of the buttress by the exterior portions of the buttress. The interior regions consequently remain open and act as a passage for the transport of fluid.

Figure 6A:
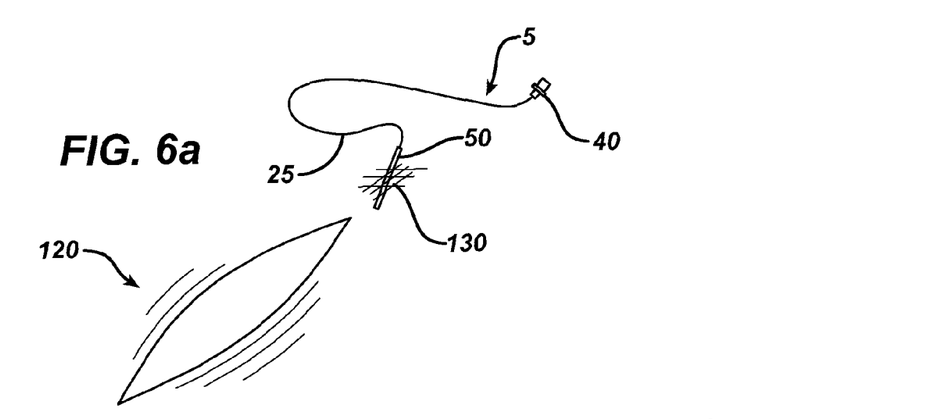
Figure 6B:
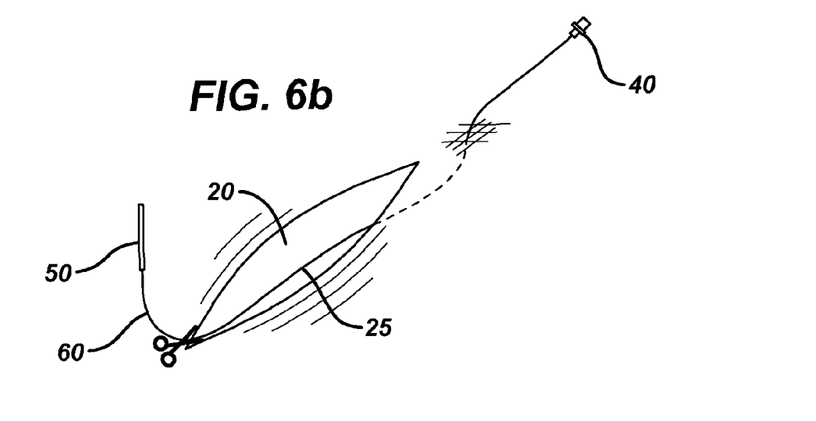
Figure 6C:
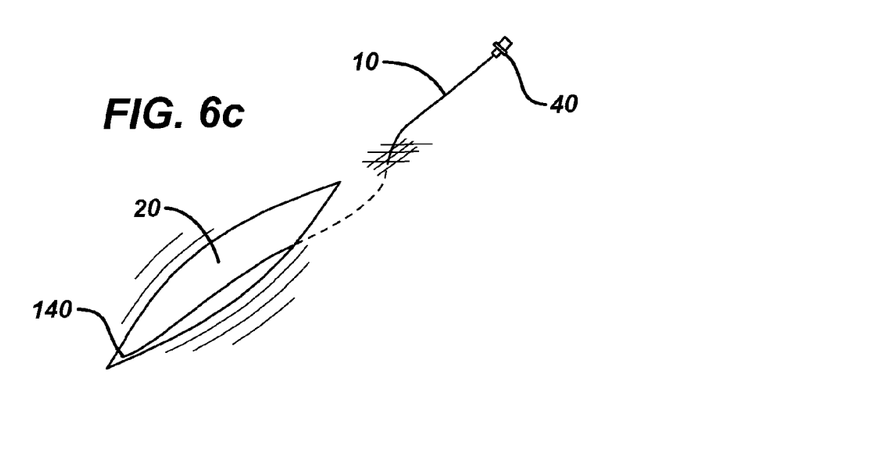

The device may be implanted in a number of ways, including but not limited to, within a surgical site along an incision plane, into tissue adjacent to the surgical incision, or through exterior tissues and into a body cavity. A method for the implantation of the device in a surgical incision is depicted in FIGS. 6a, b, and c. After an incision has been made and a surgical procedure has been performed, but before subcutaneous and dermal closure, the skin of a patient and subcutaneous tissue adjacent to the proximal end of the incision is penetrated with the suture needle that is attached to the distal end of the infusion device. The needle and distal portion of the device is then driven through the tissue and into the surgical incision until the tissue-buttressing portion 25 containing channel 20 is positioned entirely within the incision and is visible to the surgeon; and leaving at least a section of the proximal end portion 15 external to the entry point in the skin. The device may be secured in the wound by tying at least one knot 140 in the fluid-buttressing portion 25 or the optional distal end potion 35. Any excess of the tissue-buttressing portion 25 and optional distal end portion 35, including the suture needle, is then removed from the patient by cutting it away with scissors or other appropriate surgical instrument. The wound is then closed using any of the various devices and techniques used in the practice of medicine for wound closure. A therapeutic fluid may then be delivered from an external source such as an infusion pump or syringe through the optional adapter 40, through the proximal end portion 15 containing the continuous cylindrical sidewall 10, into the tissue-buttressing portion 20 and into the wound site. It is important to note that with this method, the infusion device does not enter the wound through the incision in the skin, but rather enters through by first passing through the skin and subcutaneous tissue away from the incision. With this approach, the risk of infection due to transport of bacteria along the periphery of the catheter is considered by the medical community to be less severe. Fixation of the device in the wound may be facilitated at two locations. A series of knots may be tied in the in the fluid-buttressing portion 25 or the optional distal end potion 35 of the implanted device. An additional degree of fixation occurs in the tissue between the entry point of the device at the skin surface and the subcutaneous tissue leading up to the incision. If the device is subject to an accidental tugging force as may occur if the patient snags the proximal end portion 15 of the infusion device on any number of objects, the device will be pulled out through the entry site resulting in limited trauma to the tissue surrounding the incision.

Figure 7A:
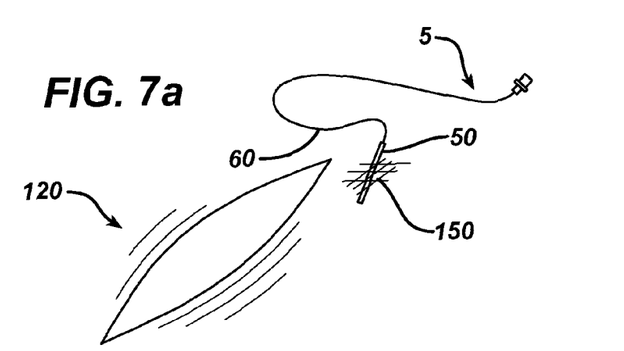
Figure 7B:
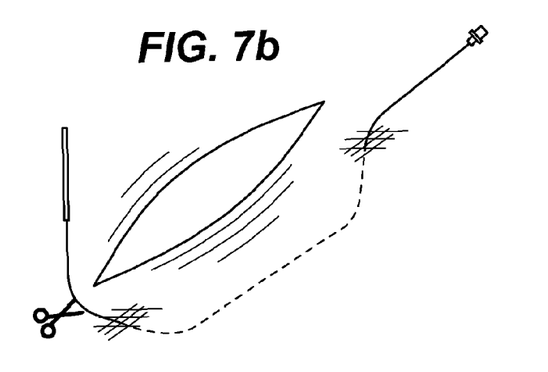
Figure 7C:
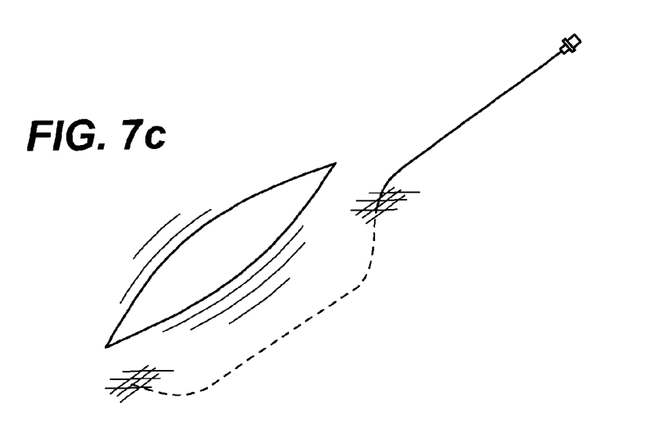

Referring now to FIGS. 7a-7c, the device may be implanted into the tissue adjacent to a wound, but not actually within the surgical incision 120. After an incision has been made and a surgical procedure has been performed, the skin of a patient and subcutaneous tissue adjacent to the proximal end of the incision is penetrated with the suture needle attached to the distal end of the device. The needle is then driven through the skin and into the tissue where the device is to be implanted 150. The needle is then threaded out through the tissue and skin at a position other than the entry point, but preferably adjacent to the distal end of the surgical incision. This pulls the proximal end of the tissue-buttressing portion 25 of the device into the tissue and slightly past the location within the tissue where infusion of the therapeutic fluid is desired. Once positioned, the portion of the distal end of the device that extends outside the body of the patient is then trimmed so that it is flush with the skin surface. Optionally, the proximal end of the device may then be pulled to cause the distal end of the device to go beneath the surface of the skin and position the tissue buttressing portion at its intended location. This same method may be applied in tissue that is not adjacent to a wound. The needle may be used to guide the device through and between the various tissue layers including, peritoneum-fascial planes, fascia-subcutaneous tissues, or subcutaneous-skin tissue.

Alternatively, the device may have perforations in portion 25, and/or may be utilized to drain bodily fluids from a wound or tissue site after the device has been installed with some or all of portion 25 located at a wound or tissue site, via the proximal end portion 15 that is external to the skin and connected directly or indirectly to a suction device.

What is claimed is:

1. A method of introducing fluid to a tissue site in tissue in a patient, comprising the steps of: 1) piercing the tissue in or in proximity to the tissue site with a surgical needle that is attached to a first distal end portion of an elongate flexible tubular member, the elongate flexible tubular member comprising a second hollow tubular proximal end portion having a continuous side wall, the first distal end portion, and a tissue-buttressing portion having an external surface, located between the first and second end portions, wherein the tissue buttressing portion has a length and comprises a fiber bundle, wherein the fiber bundle has a plurality of solid fibers in fluid communication with the second proximal end portion to allow fluid to be emitted there from along the length at a location adjacent to the wound site; 2) advancing the surgical needle and elongate flexible tubular member into tissue in or in proximity to the tissue site so that at least a portion of the tissue buttressing portion of the elongate flexible tubular member is in or in proximity to the tissue site and the proximal end portion is at least in part external of the tissue, and forming an infusion passage between the external surface of the tissue buttressing portion and abutting tissue; 3) removing the surgical needle from the distal end portion; and, 4) supplying pressurized fluid to the infusion passage and the tissue site via the tubular proximal end portion and the tissue buttressing portion.

2. The method of claim 1, further comprising the step of securing the elongate flexible tubular member with one or more knots in or in proximity to the tissue site.

3. The method of claim 1, wherein the elongate flexible tubular member comprises one or more polymers selected from the group consisting of polyglycolic acid (PGA), polylactic acid (PLA), PGA/PLA copolymers, polycaprolactone (PCL), PCUPGA copolymers, polydioxanone, trimethylcarbonate (TMC), polyproylene, polyamide, polytetraflouroethylene (PTFE), and polyethylene.

4. The method of claim 3, wherein the elongate flexible tubular member comprises an absorbable polymer.

5. The method of claim 1, wherein the diameter of the elongate flexible tubular member has a diameter along each portion of from about 0.005" to about 0.030".

* * * * *